United States Patent [19]

Lin et al.

[11] Patent Number: 4,918,222

[45] Date of Patent: Apr. 17, 1990

[54] PROCESS FOR SYNTHESIS OF N-ACETYLGLYCINE

[75] Inventors: Jiang-Jen Lin, Round Rock; John F. Knifton; Ernest L. Yeakey, both of Austin, all of Tex.

[73] Assignee: Texaco Inc., White Plains, N.Y.

[21] Appl. No.: 83,397

[22] Filed: Aug. 10, 1987

Related U.S. Application Data

[63] Continuation-in-part of Ser. No. 635,077, Jul. 27, 1984, abandoned.

[51] Int. Cl.$^4$ .................. C07C 102/00; C07C 103/50; C07C 103/48
[52] U.S. Cl. .................................... 562/518; 564/132; 564/159
[58] Field of Search .................................. 562/518, 575

[56] References Cited

U.S. PATENT DOCUMENTS

3,213,155 10/1965 Schriesheim et al. ............... 562/544
3,766,266 10/1973 Wakamatsu et al. ............... 562/518

FOREIGN PATENT DOCUMENTS

1326014 8/1973 United Kingdom ............... 562/519

Primary Examiner—Vivian Garner
Attorney, Agent, or Firm—Jack H. Park; Kenneth R. Priem; Cynthia L. Kendrick

[57] ABSTRACT

An N-acetylglycine is manufactured by reacting paraformaldehyde with an acetamide and carbon monoxide in the present of a cobalt-containing catalyst promoted by a sulfoxide or dinitride compounds. The presence of sulfoxide or dinitrile ligands are essential for the high yield synthesis of N-acetylglycine and good cobalt recovery.

1 Claim, No Drawings

PROCESS FOR SYNTHESIS OF N-ACETYLGLYCINE

CROSS-REFERENCE

This application is a continuation-in-part of U.S. patent application Ser. No. 06/635,077 filed July 27, 1984, which will be abandoned.

FIELD OF THE INVENTION

This invention relates to the improved catalyst system for amidocarbonylation of paraformaldehyde in the presence of acetamide in order to obtain N-acetylglycine.

More particularly this invention is an improved process for the production of N-acetylglycine, a possible intermediate for phenylalanine (a aspartame precursor) or for glycine production, wherein paraformaldehyde is reacted with acetamide, carbon monoxide and hydrogen in the presence of a cobalt-containing compound in a complex at a defined ratio of certain nitrile or sulfoxide promoters and a solvent, at a temperature of about 50° to about 150° C. and a pressure of 1000 to about 4000 psi, for a period of from 1 to 10 hours. The improvement of this catalyst combination resides in the fact that the active cobalt catalyst can be maintained in the solvent medium, the cobalt can be released from the solid form of N-acetylglycine-metal complex and ultimately a significantly higher yield of N-acetylglycine can be obtained than when using the cobalt catalyst alone.

BACKGROUND OF THE INVENTION

N-acetylglycine is an important chemical building block for many chemical products, such as glycine, aspartame and other amino acids. More specifically, N-acetylglycine can be the intermediate for phenylalanine synthesis via reactions with benzaldehyde, followed by hydrolysis and selective hydrogenation of an acetaminocinnamic acid intermediate (Chemical Marketing Reporter, May 14, 1984).

The synthesis of N-acetyl-α-amino acid from aldehyde and carbon monoxide was first reported by Wakamatsu, in Chemical Communication, 1540, (1970) and U.S. Pat. No. 3,766,266. This patent teaches the use of paraformaldehyde, acetaldehyde, propionaldehyde, i-butyraldehyde, phenylacetaldehyde, β-cyanopropionaldehyde etc. as reactants. The amide included in a formyl group and a carbamoyl group having at least one active hydrogen atom. Where paraformaldehyde was reacted with acetamide, N-acetylglycine was produced at only about 46% yield. Here there is the problem of the cobalt catalyst complexing with solid N-acetylglycine product and causing the loss of cobalt from reacting solvent medium. This disadvantage has prevented this synthesis from being commercialized. An improvement of this catalyst system would be desirable.

In amidocarbonylation, the aldehyde can be generated in situ from allyl alcohol, alkyl halide, oxiranes, alcohols and olefins followed by the reaction with amide and carbon monoxide to produce N-acyl- α-amino acid. Disclosures of such reactions can be found in Tetrahedron Letters, Vol. 23, No. 24, pp. 2491-2494, 1982; U.S. Pat. No, 3,996,288; German Offen. DE 3,242,374 and U.S. Pat. No. 4,264,515, respectively. In these references the synthesis of N-acetylglycine was not addressed. The problem of catalyst deposition on N-acetylglycine was not encountered by other amidoacid analogs.

N-acetylglycine (the smallest molecule in the amido acid family) has a melting point of 207° C. to about 209° C., which makes the distillation techniques for isolating the product impractical. This highly polar product has also strong tendency to chelate cobalt metal. Comparative Example 2 in this specification indicated >90% cobalt was deposited on the N-acetylglycine product. Therefore an improved catalyst system allowing for high-yield and exhibiting good cobalt recovery would be desirable in order to achieve commercial feasibility.

Many ligands or promoters have been used to improve the performance of cobalt catalysts.

In U. S. Pat. Nos. 4,209,467 and 3,996,164, amine ligands including pyridine, 2-hydroxypyridine and cycloaliphatic amines were employed with dicobalt octacarbonyl for hydroformylation or carbonylation of olefins. The function of the ligands was to stabilize the catalyst and increase the product selectivity.

In. U.S. Pat. No. 3,931,332, the importance of the cobalt and diamine promoter ratio was demonstrated. Increasing the added amount of added diamine-stabilizer markedly reduced the reaction rate of hydroformylation. A smaller amount of ligand to cobalt is preferred with respect to reaction rate.

In U.S. Pat. No. 4,612,403, an organic nitrile promoter was used to improve the process of hydroformylation. In U.S. Pat. No. 4,476,326, a sulfoxide promoter was used to improve the cobalt catalyst for methanol homologation to ethanol by reactions with a $CO-H_2$ mixture.

These products are aldehydes, alcohols, esters or carboxylic acids, which are distillable and less polar than N-acetylglycine. The use of these specific promotors would not be relevant to N-acetylglycine synthesis.

The amidocarbonylation of an aldehyde, amide and carbon monoxide to form an amidoacid involves the cobalt catalyzed carbonylation of an aldehyde-acetamide adduct under unusually mild reaction temperatures (ca 120° C.) compared with cobalt-catalyzed hydroformylation carbonylation or methanol homologation. The examples in the instant invention demonstrate the importance of certain ligands for this reaction. The nature of the solid product which acts as a strong chelating agent required experimentation to find the most suitable ligands.

For comparison, succinonitrile and sulfoxide ligands aided the cobalt recovery and the product selectivity; diamine and acetonitrile (large amount used as solvent) adversely affected the reaction. Although these effects are not well understood, we believe that the suitability of ligands is dependent on the strength of the ligand to cobalt complex and on the amount of ligands used. In the process of the instant invention ligands have been relied upon which complexed with cobalt stronger than the amido acid product did and which had no deactivating ability.

Our experimental results reveal that promoters which work for oxo, carbonylation or other CO reactions could not be simply applied to amidocarbonylation. For example, amine ligands are not suitable for N-acetylglycine synthesis. Furthermore, our invention particularly deals with paraformaldehyde to N-acetylglycine synthesis. Comparative example (3) illustrates that the synthesis of N-acetylalanine from acetaldehyde, acetamide and carbon monoxide did not have the problem of cobalt deposition because it exhibits less polarity.

SUMMARY OF THE INVENTION

The instant invention is related to an improved process for the synthesis of N-acetylglycine from paraformaldehyde, acetamide and carbon monoxide using an improved catalyst system. More particularly, this invention relates to the use of a cobalt catalyst in complex with sulfoxide or certain defined dinitrile promoters. The improvements which have been demonstrated include: (a) good cobalt recovery in ligand solution and (b) high yield or selectivity for N-acetylglycine

DETAILED DESCRIPTION OF THE INVENTION

In the narrower and more preferred practice of this invention N-acylglycines are prepared from a mixture of paraformaldehyde, an amide, carbon monoxide and hydrogen by a process which comprises contacting said mixture with a catalyst system comprising a cobalt-containing compound promoted by a ligand containing (a) sulfoxide compounds or (b) dinitrile group, which is dissolved in a substantially inert solvent at a temperature of at least 50° C. and a pressure of at least 500 psi until substantial formation of the desired N-acetylglycine has been achieved.

The improved catalyst systems can be represented by the following Equation 1:

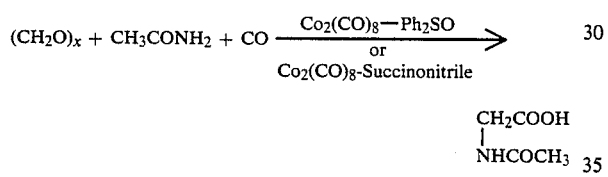

Recovery of N-acetylglycine from the reaction mixture (particularly from the cobalt catalyst) can be carried out in any convenient manner such as filtration or crystallization.

The catalyst system suitable for the practice of this invention comprises a cobalt-containing compound in a substantially inert solvent promoted by a ligand containing one or more sulfoxide or dinitrile groups.

In the catalyst system of this invention the cobalt-containing compound and the ligand-containing one or more sulfoxide or dinitrile groups are believed to be in complex equilibrium during amidocarbonylation in such a way that this catalyst system provides two important advantages over the use of cobalt alone:

(1) It gives higher yields and selectivities of N-acetyl amino acid product than can be obtained with a catalyst which utilizes solely a cobalt-containing compound dispersed in a solvent.
(2) There is greater ease of recovery of the cobalt, in solution, from the solid N-acetylglycine acid product.

The cobalt-containing compound may take many different forms. For instance, the cobalt may be added to the reaction mixture in the form of a variety of inorganic or organic cobalt salts, or cobalt carbonyls. The cobalt may, for example, be added as a cobalt halide such as cobalt bromide or cobalt chloride, or it may be added as the salt of an aliphatic or aromatic carboxylic acid such as, for example, cobalt formate, cobalt acetate, cobalt butyrate, cobalt naphthenate, and cobalt stearate. The cobalt carbonyl may be tetracobalt dodecacarbonyl or dicobalt octacarbonyl. The preferred cobalt-containing compound is dicobalt octacarbonyl.

The promoter to be used in this catalyst system may contain one or more sulfoxide groups per molecule.

The general structure of sulfoxide promoter can be described as follows:

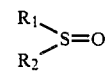

The $R_1$ and $R_2$ group can be alkyls, such as methyl, ethyl, n-butyl or n-hexyl, aromatic groups such as phenyl, chlorophenyl, aminophenyl or tolyl, arylalkyls such as benzyl or chlorobenzyl. The different $R_1$ and $R_2$ groups can also exist in the same sulfoxide molecule. Suitable examples include methyl sulfoxide, ethyl sulfoxide, n-butyl sulfoxide, methyl n-butyl sulfoxide, diphenyl sulfoxide, benzyl sulfoxide, methyl phenyl sulfoxide, 4-chlorophenyl sulfoxide, p-tolyl sulfoxide, and etc. The cyclic sulfoxide can also be used; such as tetramethylene sulfoxide.

Another group of effective promoters used in this invention to improve the cobalt catalyst comprises dinitrile compounds.

The dinitrile may be added in the form of structure A.

wherein R represent alkyl radicals such as $—(CH_2)_x—$ or aromatic groups. The preferred forms are adiponitrile, succinonitrile, glutaronitrile and ortho-phenylenediacetonitrile; mononitrile compounds such as acetonitrile, butyronitrile and benzonitrile can also be used with less satisfactory results.

As characterized above, this process is operated as a homogeneous liquid phase mixture. The reaction is preferably operated in an inert solvent. Preferred inert solvents are those which permit at least partial dissolution of the cobalt catalyst precursor, the amide and the aldehyde compound. The are generally polar solvents, for example of the ester, ether, ketone, amide, or aromatic hydrocarbon type.

Methyl and ethyl acetate are examples of suitable solvents. Other polar solvents are ethers, such as p-dioxane, methyl tertiary butyl ether, methyl tertiary amyl ether or tetrahydrofuran, tertiary amides, such as dimethyl formamide, and ethylene carbonate.

The preferred solvent is ethyl acetate.

The N-acetylglycine is often insoluble in the solvent phase. This permits separation of the cobalt catalyst which may dissolve into the solvent phase, with or without prior acidification.

The quantity of cobalt-containing compound, and promoter, and solvent to be used in the first embodiment of the invention may vary. The process is conducted in the presence of a catalytically effective quantity of the active cobalt-containing compound, promoter and solvent which gives the desired product in reasonable yield. The reaction proceeds when employing as little as about 0.1 weight percent, and even lesser amounts of the cobalt-containing compound, along with as little as about 0.1 weight percent promoter based on the total weight of the reaction mixture. The upper concentration is dictated by a variety of factors including catalyst cost, partial pressures of carbon monoxide and hydrogen, operating temperature, etc. A cobalt-containing compound concentration of from about 0.1 to about 10 weight percent in conjunction with a promoter concentration of from about 0.1 to about 10 percent, based on the total weight of the reaction mixture is generally desirable in the practice of the invention.

Particularly superior results are obtained when the above-noted components of the catalyst system are combined as follows on a molar basis: Cobalt-containing compound to promoter, 1.0:0.5 to 1.0:5.0.

The operating conditions may vary over a wide range. The reaction temperature may vary from 50° C. to 180° C. The preferred temperature is from 80° C. to 150° C. The pressure may range from 1000 psi to 4000 psi or more. It appears that higher selectivities are obtained when operating at moderate pressures, in the range from 1000 to 3500 psi.

The amidocarbonylation reaction of this invention is best conducted in a carbon monoxide-rich atmosphere, although some hydrogen gas should also be present in order to achieve maximum cobalt catalyst activity. The hydrogen to carbon monoxide molar ratio in the reactor may be varied, for example, within the range from 20:1 to 1:20, but preferably it should be rich in carbon monoxide and the $H_2$ CO ratio should be in the range 1:1 to 1:5.

The carbon monoxide employed need not satisfy particular purity requirements although catalyst contaminants should be avoided if the reaction is intended to continue over an extended period. Particularly in continuous operations, but also in batch experiments, the carbon monoxide and hydrogen gas may also be used in conjunction with up to 10% by volume of one or more other gases. These other gases may include one or more inert gases such as argon, nitrogen and the like or they may include gases that may, or may not, undergo reaction under carbon monoxide hydrogenation conditions, such as carbon dioxide, hydrocarbons, such as methane, ethane, propane and the like, ethers, such as dimethyl ether, methyl ethyl ether and diethyl ether, alkanols, such as methanol, and the like.

In all these synthesis in order to achieve a high degree of selectivity the amount of carbon monoxide, paraformaldehyde and acetamide present in the reaction mixture should be sufficient to at least satisfy the stoichiometry of the desired formation of N-acetylglycine as shown in Equation I above. Excess carbon monoxide over the stoichiometric amount may be present and is desirable.

The desired product of this synthesis is N-acylglycine. Also formed are significant amounts of bisamidal, a condensation product of paraformaldehyde and acetamide. Each of these products, including byproducts can be recovered from the reaction mixture by conventional means, e.g. filtration and crystallization.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired amino acid product, and said solid material may be recovered by methods known to the art, such as filtration, recrystallization and the like. A liquid fraction containing the catalyst components may then be recycled to the reaction zone, if desired, and additional products generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analysis, or a combination of these techniques. Analysis have for the most part, been by molar weight; all temperatures are in degrees centigrade and all pressures in pounds per square inch (psi).

The yield of N-acetylglycine in each synthesis (mole %) is estimated basis Equation I using the formula:

$$\frac{\text{Moles of N-Acetylglycine Obtained}}{\text{Moles of Paraformaldehyde Charged}} \times 100\%$$

To illustrate the process of the invention, the following examples are given. It is to be understood, however, that the examples are given in the way of illustration and are not to be regarded as limiting the invention in any way. The examples are designed to demonstrate the improved process.

EXAMPLE I

A 183 ml rocking autoclave, equipped with a glass-liner, was charged with dicobalt octacarbonyl (0.34 g, 1.0 mmole), phenylsulfoxide (0.202 g, 1.0 mmole), paraformaldehyde (2.0 g, 66 mmoles), acetamide (5.9 g, 100 mmoles) and ethyl acetate (15 g). The reactor was sealed and flushed with the mixture of $CO/H_2$ (1:1 molar ratio). The system was pressured with $CO/H_2$ (1:1) to 1200 psi and then pressured with pure CO to 2300 psi, resulting in a ca. 3:1 molar ratio of CO to $H_2$. The autoclave was heated to 120° C. and held at this temperature for ~2 hours. The maximum pressure of the reactor was 2900 psi during the run. After the designated reaction time, the system was cooled to room temperature and the excess gas was vented. The resulting product materials were filtered. The solid (6.5 g) and liquid (17.9 g, brown color) materials were recovered. The H-nmr analysis showed two products, N-acetylglycine (I) and bisamidal (II) in the solid material.

The molar ratio of N-acetylglycine(I) and bisamidal-(II) in the product solid is 17.6:1.0.

The yield of N-acetylglycine(I) basis paraformaldehyde charged was 68 mole %. The yield of bisamidal-(II) was 4%.

The relative selectivity for (I) and (II) was 94 mole % versus 6 mole %.

The liquid product fraction was found to contain 5250 ppm soluble cobalt. This represents a ca. 81% recovery of cobalt in solution basis $Co_2(CO)_8$ charged.

It is of note that no significant amounts of compounds (I) and (II) can be found in the liquid product fraction. This synthesis procedure therefore allows for a relatively easy separation of N-acetylglycine product solid(I) from the soluble cobalt-containing catalyst fraction.

EXAMPLE II (Comparative)

N-Acetylglycine Synthesis by Dicobalt Octacarbonyl

A 183 ml rocking autoclave equipped with a glass-liner was charged with dicobalt octacarbonyl (0.34 g. 1.0 mmole), paraformaldehyde (2.0 g, 66 mmoles), acetamide (5.9 g, 100 mmoles) and ethyl acetate (15 g.). The reactor was sealed and flushed with the mixture of CO-$H_2$(1:1 molar ratio). The system was pressured with CO-$H_2$ (1:1 ) to 1200 psi and then pressured with pure CO to 2300 psi, resulting in a ca. 3:1 molar ratio of CO to $H_2$. The autoclave was heated to 120° C. and held at this temperature for about 2 hours. The maximum pressure of the reaction was 2675 psi during the run. After the designated reaction time, the system was cooled to room temperature and the excess gas was vented. The resulting product materials were filtered. The solid (6.5 g) and liquid (14.5 g) materials were recovered. The H-hmp analysis showed two products. N-acetylglycine (I) and bisamidal (II) in 77 to 23 molar ratio.

The yield of N-acetylglycine (I) basis paraformaldehyde was 63%.

The liquid product fraction was found to contain only <5 ppm cobalt. Over 90% cobalt charged was lost due to the depositions on solid N-acetylglycine.

EXAMPLE III (Comparative)

N-Acetylalanine Synthesis

A 183 ml rocking autoclave equipped with a glass-liner, was charged with acetaldehyde (3.0 g), acetamide (5.9 g), ethyl acetate (15 g) and dicobalt octacarbonyl (0.34 g). The reaction was sealed and flushed with the mixture of CO-$H_2$(1:1 molar ratio). The system was pressured with CO-$H_2$ (1:1 to 1200 psi and then pressured with pure CO to final pressure of 2300 psi. The autoclave was heated to 120° C. and held at this temperature for two hours. The system was allowed to cool to room temperature. The excess gas was vented. The resulting product mixture was liquid only. The cobalt analysis of this homogeneous solution was 4500 ppm (calculated 4800 ppm). The H-mmr analysis of the product solution indicated the presence of N-acetylalanine.

In comparison with N-acetylglycine synthesis, N-acetylalanine (a larger amido acid than N-acetylglycine) did not appear to exhibit the problem of cobalt deposition on solid product.

EXAMPLE IV

Using Dicobalt Octacarbonyl-Succinonitrile (1:1 ratio)

A glass-lined autoclave was charged with dicobalt octacarbonyl (0.34 g, 1.0 mmole), succinonitrile (0.08 g, 1.0 mmole), paraformaldehyde (2.0 g, 66 mmoles), acetamide (5.9 g, 100 mmoles) and ethyl acetate (15.0 g). The reaction was sealed and flushed with the mixture of CO-$H_2$(1:1 molar ratio) then pressured with CO-$H_2$ (1:1) to 1200 psi CO to 2300 psi (resulting ca. 3:1 CO-$H_2$ mixture). The system was heated to 120° C. and the maximum pressure of 3000 psi was recorded during this process. The reaction was run for 2 hours; then the reactor cooled to room temperature and the excess gas was vented. The product material was filtered. The H-nmr showed two products: N-acetylglycine (1) (81% yield basis on paraformaldehyde charged) and bisamidal, (2), (6% yield).

The cobalt analysis of the liquid showed 3470 ppm concentration, 47% cobalt recovered basis dicobalt octacarbonyl charged.

EXAMPLE V

Using Dicobalt Octarcarbonyl-Succinonitrile (1:3 Ratio)

The experimental procedures of Example V were repeated, except charging dicobalt octacarbonyl (00.34 g. 1 mmole), succinonitrile (0.24 g, 3.0 mmoles), paraformaldehyde (2.0 g 66 moles), acetamide (5.9 g 100 mmoles) and ethyl acetate (15 g). The reaction conditions were 2400 psi of CO-$H_2$(3:1 molar ratio), 120° C. and 2 hours. The yield for N-acetylglycine (solid) was 78%. The yield for bisamidal byproduct was 0%. The cobalt recovery in liquid layer was 76%. It is noted that: (A) good cobalt recovery was obtained; (B) there was a high yield of N-acetylglycine with no byproduct.

EXAMPLE VI (Comparative)

With Dicobalt Octacarbonyl-Amine Ligand

The experiment of Example V was repeated, except the reactor was charged with dicobalt octacarbonyl (0.34 g 1 mmole) and TMEDA (tetramethylene diamine 0.116 g, 1 mmole) paraformaldehyde (2 g), acetamide (5.9 g) and ethyl acetate (15 g). The conditions were 2900 psi CO-$H_2$, 120° C. and 2

2 (3:1 molar ratio) hours. The result was no N-acetylglycine. The TMEDA amine ligand deactivated the N-acetylglycine synthesis, although amine might be a good ligand to use with cobalt for other reactions (e.g. hydroformylation and carbonylation).

What is claimed is:

1. A process for synthesizing N-acetylglycine exhibiting improved release of cobalt from the solid form of N-acetylglycine-metal complex and a higher yield of N-acetylglycine which comprises:

reacting paraformaldehyde, carbon monoxide, hydrogen and acetamide with a catalyst comprising a cobalt-containing compound in complex with a dinitrile promoter from the group consisting of adiponitrile, succinonitrile or glutaronitrile in an ethyl acetate solvent at a temperature of 80° C. to 150° C. and a pressure of 1000 psi to 4000 psi at a cobalt-containing compound to promoter molar ratio of 1.0:05 to 1:0:5.0.

* * * * *